US006395269B1

(12) United States Patent
Fuller et al.

(10) Patent No.: US 6,395,269 B1
(45) Date of Patent: May 28, 2002

(54) SUNSCREEN LOTION OR SPRAY COMPOSITION

(75) Inventors: Jennifer Fuller, Mahwah, NJ (US); James Sanogueira, Suffern, NY (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/640,099

(22) Filed: Aug. 15, 2000

Related U.S. Application Data
(60) Provisional application No. 60/149,090, filed on Aug. 16, 1999.

(51) Int. Cl.$^7$ .............................. A61K 7/42; A61K 7/44; A61K 7/00
(52) U.S. Cl. ........................ 424/89; 424/60; 424/400; 424/401
(58) Field of Search ............................ 424/89, 60, 400, 424/401

(56) References Cited

U.S. PATENT DOCUMENTS

| 4,144,325 | A | | 3/1979 | Voyt .............................. 424/59 |
|---|---|---|---|---|
| 4,954,332 | A | | 9/1990 | Bissett et al. .................. 424/59 |
| 4,975,272 | A | | 12/1990 | Voyt .............................. 424/59 |
| 5,208,011 | A | | 5/1993 | Vaughan ....................... 424/59 |
| 5,445,815 | A | | 8/1995 | Siegfried ...................... 424/59 |
| 5,609,854 | A | | 3/1997 | Guerrero et al. .............. 424/59 |
| 5,663,213 | A | | 9/1997 | Jones et al. .................. 523/105 |
| 5,709,847 | A | | 1/1998 | Bissett et al. .................. 424/59 |
| 5,753,243 | A | | 5/1998 | Cunningham et al. ...... 424/401 |
| 5,766,575 | A | | 6/1998 | Crotty et al. .................. 424/59 |
| 5,770,183 | A | | 6/1998 | Linares ......................... 424/59 |
| 5,811,112 | A | | 9/1998 | Chandar et al. ............. 424/401 |
| 6,190,645 | B1 | * | 2/2001 | Sanogueira et al. .......... 424/59 |

* cited by examiner

Primary Examiner—Shelley A. Dodson
(74) Attorney, Agent, or Firm—Ohlandt, Greeley, Ruggiero & Perle, LLP

(57) ABSTRACT

The present invention is a sunscreen composition that can interchangeably be used as a lotion or as a spray, without any change to the composition. The composition contains a sunscreen agent, a rheological additive, a pH adjuster, and water. Optionally, the sunscreen composition may include an emulsifier, an emollient, a moistening agent, a waterproofing agent, and a preservative.

20 Claims, No Drawings

SUNSCREEN LOTION OR SPRAY COMPOSITION

This application claims benefit of provisional No. 60/149,090 filed Aug. 16, 1999.

BACKGROUND OF THE INVENTION

I. Field of the Invention

The present invention relates to sunscreen. More particularly, the present invention relates to sunscreen that are applied as a lotion or as a spray.

II. Description of the Prior Art

Sunscreen compositions are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. Ultraviolet rays at a wavelength of 320 nm to 400 nm, known as UV-A radiation, produces tanning of the skin. However, in the process of doing so, the UV-A rays can damage or harm the skin.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

As stated above, sunscreens are typically formulated with the goal of inhibiting skin damage from the sun's rays. The sunscreen composition filters or blocks the harmful UV-A and UV-B rays that can damage and harm the skin. It is believed that sunscreen agents accomplish this by absorbing the UV-A and/or UV-B rays.

In general, sunscreen compositions are oil in water emulsions. In this system, the UV-absorbing compounds are typically incorporated into the oil phase.

Consumers consider many factors when purchasing a sunscreen product. One of the most important considerations is the sun protection factor (SPF). This determines the amount of protection that the sunscreen composition provides over a given period of time. There are many to choose from and selection will be based upon the consumer's needs. The consumer also gives consideration to the substantivity of the product, that is how durable is the product after applying it over the skin. This affects how often the composition will need to be applied when the consumer is out in the sun. A third consideration is product feel and how well the product spreads over the skin. Typically, consumers want a product that feels smooth and silky and can be applied in a smooth, continuous film over the skin. Another factor is the shelf life of the product, which is determined by the chemical and physical stability of the sunscreen composition. In addition, product form will also play a part since there is a variety of choices such as lotions, gels, creams, and sprays which are available. Form preference could ultimately determine whether the consumer decides to purchase the product.

Most sunscreen compositions are formulated for use as a lotion. The consumer would squeeze the lotion out of the package and rub the sunscreen composition over the skin. However, the use of sunscreens in a spray form is gaining popularity. But, a formulation made to be applied as a lotion cannot be used in a spray vehicle without modification and reformulation. This requires product reformulation, which requires time and money.

A composition that is capable of functioning as a lotion or a spray is desirable. This would save time in formulation development costs and would improve manufacturing efficiencies. For instance, the same raw materials would be used in the lotion and spray, thus potentially reducing raw material and storage costs.

BRIEF SUMMARY OF THE INVENTION

It is an object of the present invention to provide a sunscreen composition that can be effectively applied as a lotion.

It is also an object of the present invention to provide such a sunscreen composition that can also be effectively applied as a spray.

It is another object of the present invention to provide such a sunscreen composition that either as a lotion or spray spreads uniformly over the skin.

It is yet another object of the present invention to provide such a sunscreen composition that reduces viscosity as it is sheared in order that the composition may be used as a lotion or a spray.

To accomplish the foregoing objects and advantages, the present invention, in brief summary, is a sunscreen composition that can conveniently be used as a lotion or a spray, without any change to the composition. The composition has a sunscreen agent, a rheological additive, a pH adjuster, and water. In a preferred embodiment, the sunscreen composition also contains an emulsifier, an emollient, a moistening agent, a waterproofing agent, and/or a preservative.

DETAILED DESCRIPTION OF THE INVENTION

The present invention is a sunscreen composition that can conveniently be used interchangeably as a lotion or a spray, without having to change the composition. The composition includes (a) a sunscreen agent, (b) a rheological additive, (c) water, and (d) a pH adjuster.

The sunscreen composition of the present invention is thixotropic. That is, its viscosity significantly decreases when shear forces are applied. This unique characteristic enables the composition of the present invention to be used as a lotion or spray. As a lotion, the composition can be easily poured from the package and spread over the skin. The same composition in a spray form, is sheared as it is dispensed through the spray mechanism, which promotes the flow of the composition out of the package.

One or more sunscreen agents that can be used in the present invention must be capable of absorbing or blocking the harmful effects of ultraviolet radiation. In addition, they must be non-toxic and non-irritating when applied to the skin. For example, suitable sunscreen agents include but are not limited to para-aminobenzoic acid (PABA), avobenzone, benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, and mixtures thereof. The preferred sunscreen agents are avobenzone, benzophenone-3, octyl methoxycinnamate, octyl salicylate, homosalate, and mixtures thereof.

The sunscreen agent is included in the formulation at about 1 percentage by weight or weight percent (wt.%) to about 40 wt. % of the total composition. The amount of sunscreen agents in the composition will vary in the above range dependent upon the sun protection factor (SPF) desired. The higher the SPF, the greater the total amount of sunscreen agents. Preferably, the sunscreen agents are included at about 4 wt. % to about 35 wt. % to achieve a SPF of 2 to 50.

The composition of the present invention includes a rheological additive, which imparts thixotropic properties to the present composition. This enables it to flow as a lotion or be dispensed in a spray. The key feature of the rheological additive is that it changes the behavior of the present composition when shear forces are applied, enabling the present composition to readily flow. A suitable rheological additive includes, for example, an acrylates/steareth-20 methacrylate copolymer sold under the tradename ACULYN 22 by ISP/Rohm & Haas. In addition to controlling the rheology of the finished product, this component also emulsifies the oil phase.

One or more rheological additives are included in a total amount about 0.2 wt. % to about 2.8 wt. % in the composition of the present invention. Preferably, about 0.5 wt. % to about 1.5 wt. % of rheological additives are used in the present composition.

The composition of the present invention also has water. Water is present in an amount about 45 wt. % to about 95 wt. %, preferably, about 50 wt. % to about 75 wt. %.

The pH of the composition of the present invention is adjusted by one or more basic pH adjusters or chelating agents, which neutralize and activate the rheological additive. For example, sodium hydroxide, triethanolamine, trisodium ethylenediaminetetraacetic acid, and mixtures thereof are suitable pH adjusters in the present invention.

An effective amount of a pH adjuster is included to adjust the pH of the final composition to about 6.0 to about 7.8. Preferably, the pH is adjusted to about 6.3 to about 7.3.

An emulsifier is optionally included in the composition of the present invention. The emulsifier enables two or more immiscible liquids to be combined homogeneously, while increasing the viscosity of the composition. Moreover, an emulsifier acts to stabilize the composition.

One or more emulsifiers that can be used in the present invention include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate, and mixtures thereof. The preferred emulsifier is sorbitan oleate.

The amount of emulsifier is about 0.1 wt. % to about 1.0 wt. % in the composition of the present invention. Preferably, one or more emulsifiers in an amount about 0.1 wt. % to about 0.4 wt. % of the total composition is used.

Furthermore, one or more synthetic polymers may be used as an emulsion stabilizer. For example, PVP Eicosene copolymer, PEG-22/dodecyl glycol copolymer, PEG-45/dodecyl glycol copolymer, and mixtures thereof.

The present composition may additionally contain other ingredients, such as one or more emollients. An emollient provides a softening or soothing effect on the skin surface and is generally considered safe for topical use. It also helps control the rate of evaporation and the tackiness of the composition.

Preferred emollients include, but are not limited to, mineral oil, lanolin oil, coconut oil, cocoa butter, olive oil, aloe extracts such as aloe vera, jojoba oils, castor oil, fatty acids such as oleic and stearic, fatty alcohols such as cetyl and hexadecyl (ENJAY), diisopropyl adipate, hydroxybenzoate esters, benzoic acid esters of $C_9$–$C_{15}$ alcohols, isononyl isononanoate, alkanes such as mineral oil, silicones such as dimethyl polysiloxane, ether such as polyoxypropylene butyl ethers and polyoxypropylene cetyl ethers, and $C_{12}$–$C_{15}$ alkyl benzoate. The most preferred emollient is $C_{12}$–$C_{15}$ alkyl benzoate.

The total amount of emollient is typically about 2 wt. % to about 20 wt. % of the total weight of the present composition. The preferred amount of emollient is about 2 wt. % to about 15 wt. %, and most preferably about 4 wt. % to about 10 wt. %.

A moistening agent, such as a humectant, may be used in the composition of the present invention. Suitable humectants include but are not limited to glycerin, polyethylene glycol, polypropylene glycol, sorbitol, PEG-4, and mixtures thereof.

One or more moistening agents are optionally included at a total amount about 0.25 wt. % to about 5 wt. % of the present composition. Preferably, about 0.5 wt. % to about 2 wt. % of one or more moistening agents may be used.

Another optional ingredient is a waterproofing agent. The waterproofing agent is a hydrophobic material that imparts film forming and waterproofing characteristics to the emulsion. One such agent is $C_{30}$–$C_{38}$ olefin/isopropyl maleate/MA copolymer, which is available from New Phase Technologies as PERFORMA V 1608. One or more waterproofing agents may be in the composition of the present invention in an amount about 0.5 wt. % to about 5 wt. %.

Optionally, one or more preservatives may be included in the composition of the present invention. The preservative protects the composition from microbial contamination and/or oxidation. As such, the preservatives can include antioxidants. Preservatives such as diazolidinyl urea, iodopropynl butylcarbamate, vitamin E and its derivatives including vitamin E acetate, vitamin C, butylated hydroxytoluene, methylparaben, and mixtures thereof may be included as a preservative/antioxidant.

About 0.5 wt. % to about 1.5 wt. % of preservative may be included in the composition of the present invention. Preferably, one or more preservatives total about 0.5 wt. % to about 1 wt. % of the total weight of the present composition.

The sunscreen composition of the present invention may also contain optional additives. For instance a fragrance, colorant, plant extract, absorbent, and mixtures thereof may be added.

The components of the present invention may be combined to form a stable oil in water emulsion. The sunscreen is to incorporated into the oil phase and later combined with water with the help of an emulsifier.

The process used to manufacture the composition of the present invention must be capable of forming a homogeneous composition that can be spread into a film.

The composition may be prepared by using techniques and methods well known in the art. In general, ingredients are incorporated by mixing and applying heat if necessary, until the composition is uniform and homogeneous. The composition may be homogenized to ensure homogeneity and to build the proper viscosity.

The sunscreen composition of the present invention is then packaged in a bottle as a lotion or may be incorporated into a pump spray bottle. Thus, the present sunscreen composition provides for its interchangeable use as a lotion to be poured or a pump spray, without any change to the composition itself.

In a preferred embodiment, the present invention is a sunscreen composition for use as a lotion or spray. The composition has about 1 wt. % to about 40 wt. % sunscreen agent, about 0.2 wt. % to about 2.8 wt. % rheological additive, about 45 wt. % to about 95 wt. % water, and an effective amount of a pH adjuster in which the pH of the final composition is about 6 to about 7.8. Also, it is preferred that the sunscreen composition include about 0.1 wt. % to about 1 wt. % emulsifier. In an even more preferred sunscreen composition, there is included about 2 wt. % to about 20 wt. % emollient, about 0.25 wt. % to about 5 wt. % moistening agent, about 0.5 wt. % to about 5 wt. % waterproofing agent, and about 0.5 wt. % to about 1.5 wt. % preservative.

Having thus described the present invention with particular reference to preferred embodiments thereof, it will be apparent that various changes and modifications may be made therein without departing from the spirit and scope of the present invention as defined in the appended claims.

What is claimed is:

1. A sunscreen composition that can be used interchangeably as a lotion or spray without any change to the composition, the composition comprising:
   (a) a sunscreen agent;
   (b) a rheological additive;
   (c) a pH adjuster; and
   (d) water.

2. The composition of claim 1, wherein said sunscreen agent is selected from the group consisting of avobenzone, benzophenone-3, octyl methoxycinnamate, octyl salicylate, homosalate, and mixtures thereof.

3. The composition of claim 1, wherein said sunscreen agent is about 1 wt. % to about 40 wt. % of the total weight of the composition.

4. The composition of claim 1, wherein said rheological additive is an acrylates/steareth-20 methacrylate copolymer.

5. The composition of claim 1, wherein said rheological additive is about 0.2 wt. % to about 2.8 wt. %.

6. The composition of claim 1, wherein said pH adjuster is selected from the group consisting of sodium hydroxide, trisodium ethylenediaminetetraacetic acid, and mixtures thereof.

7. The composition of claim 1, wherein said pH adjuster is included in an effective amount to adjust the pH to about 6 to about 7.8.

8. The composition of claim 1, further comprising an emulsifier.

9. The composition of claim 8, wherein said emulsifier is sorbitan oleate.

10. The composition of claim 8, wherein said emulsifier is present in an amount about 0.1 wt. % to about 1 wt. %.

11. The composition of claim 1, further comprising an emollient.

12. The composition of claim 11, wherein said emollient is selected from the group consisting of a $C_{12}$–$C_{15}$ alkyl benzoate, aloe vera, and mixtures thereof.

13. The composition of claim 1, further comprising a moistening agent.

14. The composition of claim 10, wherein said moistening agent is a humectant.

15. The composition of claim 1, further comprising a waterproofing agent.

16. The composition of claim 10, wherein said waterproofing agent is $C_{30}$–$C_{38}$ olefin/isopropyl maleate/MA copolymer.

17. A sunscreen composition that can be used as a lotion or spray that exhibits a thixotropic rheology, comprising:
   (a) about 1 wt. % to about 40 wt. % sunscreen agent;
   (b) about 0.2 wt. % to about 2.8 wt. % rheological additive;
   (c) about 45 wt. % to about 95 wt. % water; and
   (d) an effective amount of a pH adjuster,
   wherein the pH of the composition is about 6 to about 7.8.

18. The composition of claim 17, further comprising an emulsifier.

19. The composition of claim 17, further comprising an emollient, a moisturizing agent, and a waterproofing agent.

20. A sunscreen composition for use as a lotion or spray that exhibits thixotropic rheology, comprising:
   (a) a sunscreen agent;
   (b) a rheological additive;
   (c) a pH adjuster;
   (d) an emulsifier;
   (e) an emollient;
   (f) a moistening agent;
   (g) a preservative;
   (h) a waterproofing agent; and
   (i) water.

* * * * *